(12) United States Patent
Hughes

(10) Patent No.: US 12,740,772 B2
(45) Date of Patent: Sep. 22, 2026

(54) LABORATORY SAMPLE CARRIER

(71) Applicant: PYRAMID INNOVATION LTD, Polegate (GB)

(72) Inventor: Thomas Fergus Hughes, Netherfield (GB)

(73) Assignee: PYRAMID INNOVATION LTD, Polegate (GB)

( * ) Notice: Subject to any disclaimer, the term of this patent is extended or adjusted under 35 U.S.C. 154(b) by 911 days.

(21) Appl. No.: 17/610,070

(22) PCT Filed: May 5, 2020

(86) PCT No.: PCT/GB2020/051101
§ 371 (c)(1),
(2) Date: Nov. 9, 2021

(87) PCT Pub. No.: WO2020/225550
PCT Pub. Date: Nov. 12, 2020

(65) Prior Publication Data

US 2022/0225968 A1 Jul. 21, 2022

(30) Foreign Application Priority Data

May 9, 2019 (GB) ..................................... 1906544

(51) Int. Cl.
*A61B 10/00* (2006.01)
*B01L 3/00* (2006.01)
(Continued)

(52) U.S. Cl.
CPC .......... *A61B 10/0096* (2013.01); *B01L 3/508* (2013.01); *B01L 3/545* (2013.01);
(Continued)

(58) Field of Classification Search
CPC ........... A61B 10/0096; B01L 2200/025; B01L 2300/021; B01L 3/508; B01L 3/545;
(Continued)

(56) References Cited

U.S. PATENT DOCUMENTS

2003/0044969 A1* 3/2003 Shin ...................... B01L 3/5085 435/303.1
2007/0104618 A1* 5/2007 Williamson ............ B01L 3/545 422/400
(Continued)

FOREIGN PATENT DOCUMENTS

CN 1898022 A * 1/2007 .............. B01L 3/545
JP H0161659 U * 4/1989
(Continued)

OTHER PUBLICATIONS

CN-1898022-A English translation (Year: 2025).*
(Continued)

*Primary Examiner* — Jennifer Wecker
*Assistant Examiner* — Jonathan Bortoli
(74) *Attorney, Agent, or Firm* — Lippes Mathias LLP

(57) ABSTRACT

A laboratory sample cassette (1) comprises a main body (2) having a writing surface (3), and at least two protrusions (14) extending from the writing surface (3). Each said protrusion (14) has substantially the same height from the writing surface (3).

13 Claims, 5 Drawing Sheets

(51) Int. Cl.
*C12M 1/16* (2006.01)
*G01N 1/36* (2006.01)

(52) U.S. Cl.
CPC ................. *C12M 1/16* (2013.01); *G01N 1/36* (2013.01); *B01L 2200/025* (2013.01)

(58) Field of Classification Search
CPC .... B01L 3/50; B01L 3/54; C12M 1/16; G01N 1/36; G01N 1/31
See application file for complete search history.

(56) References Cited

U.S. PATENT DOCUMENTS

| | | | | |
|---|---|---|---|---|
| 2007/0140920 | A1* | 6/2007 | McCormick | G01N 1/36 422/400 |
| 2007/0166834 | A1* | 7/2007 | Williamson | G01N 1/36 436/174 |
| 2008/0227144 | A1* | 9/2008 | Nightingale | G01N 1/312 435/40.52 |
| 2010/0190205 | A1 | 7/2010 | Guo et al. | |
| 2011/0129956 | A1* | 6/2011 | Polito | H01L 31/0236 257/E31.13 |
| 2013/0022518 | A1 | 1/2013 | Park et al. | |
| 2013/0162744 | A1* | 6/2013 | Hughes | B41M 5/0256 347/110 |
| 2015/0087018 | A1* | 3/2015 | Webber | G01N 1/36 435/40.5 |
| 2016/0216176 | A1 | 7/2016 | Knorr et al. | |

FOREIGN PATENT DOCUMENTS

| | | |
|---|---|---|
| JP | 2019 020202 | 2/2019 |
| WO | WO 2009/061680 A1 | 5/2009 |

OTHER PUBLICATIONS

JP-H0161659-U English translation (Year: 2025).*
Brady, 2013, "A Break-Through Specimen Labelling System" Available from: https://www.zoro.com/static/cms/enhanced_pdf/28dPPpgp5B_nAMSJNeyogMRTdJPWn_NveiQdgpUaXeggQ.PDF [Accessed Oct. 25, 2019] See images contained within brochure.
PCT/GB2015/052404, International Search Report and Written Opinion, Oct. 29, 2015.
GB 1415242.5 Search Report Under Section 17(5), Jan. 29, 2015.
Brady, 2013, "A Break-Through Specimen Labelling System" Available from: https://www.zoro.com/static/cms/enhanced_pdf/Z8dPPpgp5B_nAMSJNeyogMRTdJPWnNveiQdgpUaXeggQ.PDF [Accessed Oct. 25, 2019] See images contained within brochure.

* cited by examiner

LABORATORY SAMPLE CARRIER

The present invention relates to a laboratory sample cassette having a marking or writing surface.

A tissue processing laboratory sample cassette may have a writing surface disposed generally at an angle of 45° to the main body of the cassette. The main body has a recess for holding a tissue sample so that the main body forms a tray, and the tray is covered by a removable lid.

The writing surface is marked by a printer, such as a thermal printer, with details of a tissue sample to be put in the tray. After the tissue sample is put in the tray, the lid is placed over the tray and the laboratory sample cassette is processed. This includes an embedding process wherein the writing surface and other surfaces of the cassette may be at least partially covered by wax. The wax on the writing surface needs to be removed so that details of the sample printed on the writing surface are not obscured. This may be done by rubbing or holding the writing surface against a surface of a heated metal block to melt the wax from the writing surface. A problem with this is that the surface of the metal block can be abrasive which may damage the sample details printed on the writing surface making the sample details unreadable.

It is an object of the present invention to provide a laboratory sample cassette that alleviates the above-mentioned problem.

According to one aspect of the present invention there is provided a laboratory sample cassette comprising a main body having a writing surface, and at least two protrusions extending from the writing surface, each said protrusion having the same height or substantially the same height from the writing surface.

The laboratory sample cassette may be of unitary or monolithic construction.

The at least two protrusions may be configured to hold the writing surface parallel or substantially parallel to a flat surface when the laboratory sample cassette is placed against the flat surface with the writing surface facing the flat surface. Thus, the protrusions of the laboratory sample cassette enable the writing surface to be held away from the flat surface of a heated metal block so that it cannot be abraded by the metal block whilst at the same time enabling any wax on the writing surface to be melted from it. The molten wax may run off the writing surface between the protrusions. The at least two protrusions may be configured to engage the flat surface.

Each said protrusion may be adjacent at least one edge of the writing surface. Each said protrusion may have a rounded profile. This provides the advantage that tape used in the printing process, such as thermal tape, will not be damaged by the protrusions as it passes over the writing surface. The height of each said protrusion from the writing surface may be in the range of 0.05 mm to 3 mm. Such a range of heights provides an appropriate stand-off from a heated block to prevent damage to printing on the writing surface while allowing the writing surface to be close enough to the heated block to allow wax on the writing surface to be melted by radiant heat from the heated block and therefore be able to run away from the writing surface.

The writing surface may be rectangular.

There may be four said protrusions, each said protrusion being adjacent a respective corner of the writing surface and having substantially the same height from the writing surface. A print area on the writing surface for a print head of a thermal printer to print on may be defined between two said protrusions adjacent a first shorter edge of the rectangular writing surface and two said protrusions adjacent an opposite second shorter edge of the rectangular writing surface.

There may be two said protrusions, each said protrusion comprising a rib extending parallel or substantially parallel to and adjacent a respective opposite edge of the writing surface and having the same height or substantially the same height from the writing surface. The ribs may be spaced apart to define a print area on the writing surface for a print head of a thermal printer to print on. Each said rib may extend parallel or substantially parallel to and adjacent a respective shorter edge of the writing surface. Each said rib may extend parallel or substantially parallel to and adjacent a respective longer edge of the writing surface.

The protrusions may be sized and positioned to provide the maximum suitable print area.

The laboratory sample cassette including the at least two protrusions may be formed by injection moulding or may be an injection moulded cassette.

Each said protrusion may have a width at its base on the writing surface in the range of 0.1 mm to 3 mm.

The writing surface may be disposed at an inclined angle to the main body of the cassette or may be disposed at an acute angle to a bottom of the main body of the cassette.

There may be a combination of the laboratory sample cassette and the flat surface which may be heated.

According to another aspect of the present invention there is provided a method for removing wax from a writing surface of a laboratory sample cassette, comprising the steps of: (a) providing at least two protrusions which extend from the writing surface of a main body of the laboratory sample cassette, each said protrusion having the same height or substantially the same height from the writing surface; and (b) holding the laboratory sample cassette so that the protrusions engage a flat heated surface causing the writing surface to be parallel or substantially parallel to the flat surface, and enabling wax on the writing surface to be melted from the writing surface.

Step (a) may include providing the laboratory sample cassette which is of unitary or monolithic construction and includes the at least two protrusions which extend from the writing surface of the main body.

The method may include the step of marking the writing surface after step (a) and before step (b).

Embodiments of the present invention will now be described, by way of example, with reference to the accompanying schematic drawings, in which.

Figure 1:
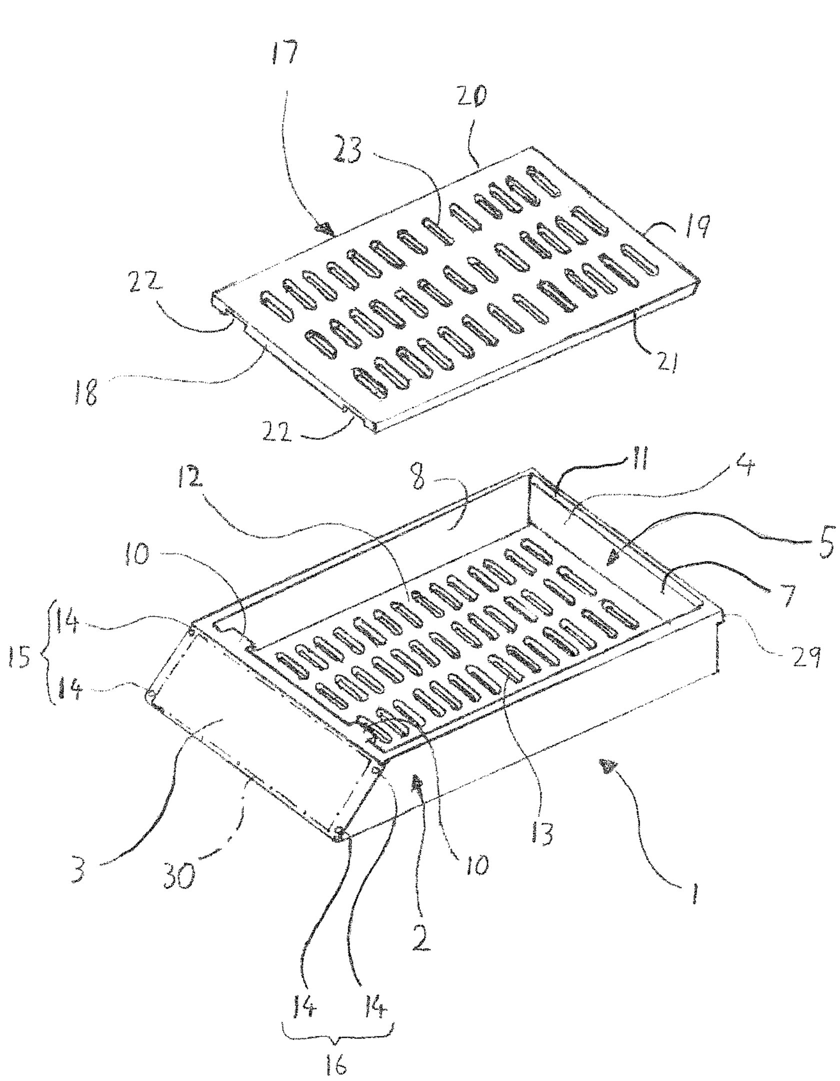
FIGS. 1 and 2 are perspective views of a laboratory sample cassette according to one embodiment of the invention, the cassette having an associated lid.
Figure 2:
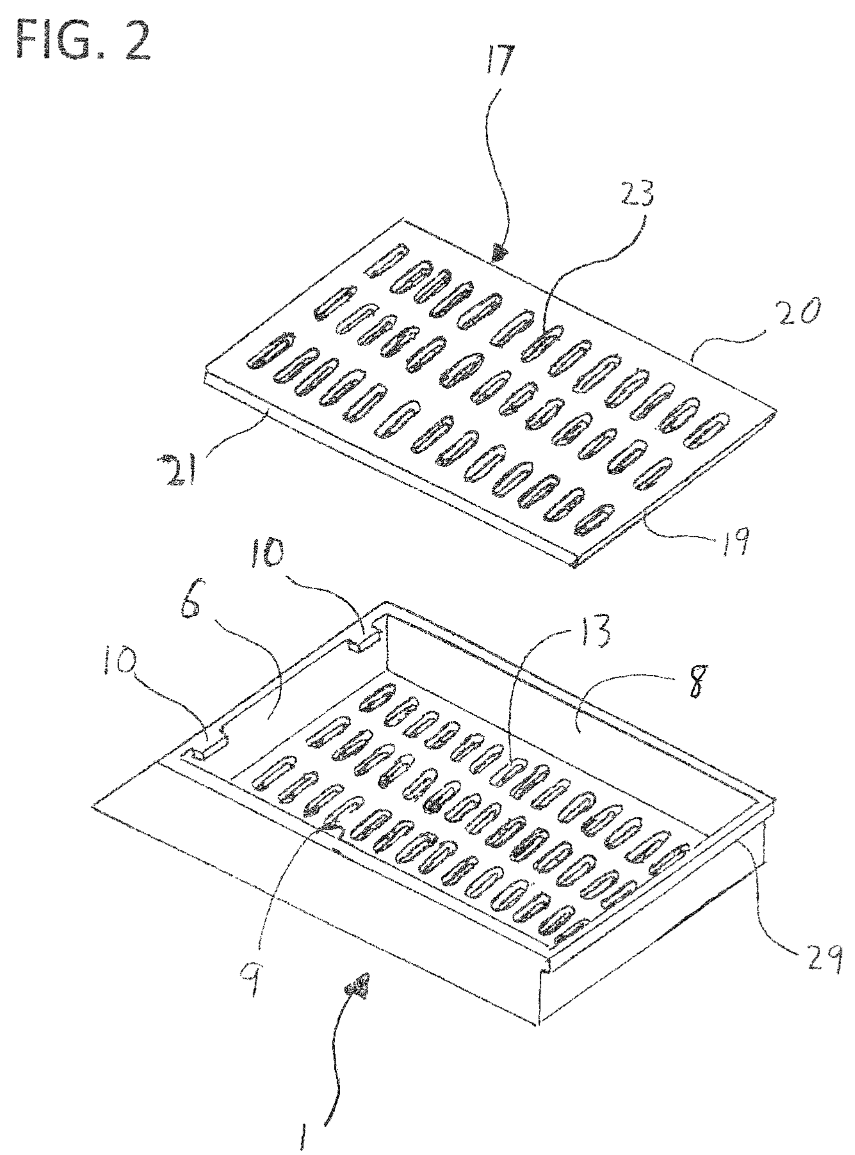

Referring to FIGS. 1 and 2 of the accompanying drawings, a laboratory sample cassette 1 has a main body 2. A rectangular writing or marking surface 3 is disposed at an inclined or acute angle to a bottom of the main body 2 of the cassette 1. The cassette 1 has a hollow space or recess 4 behind the writing surface 3 for holding a tissue sample so that the main body 2 forms a tray 5. The tray 5 has a first shorter wall surface 6 adjacent the writing surface 3 and an opposite second shorter wall surface 7, and has first and second longer wall surfaces 8, 9 facing each other. A pair of tabs 10 extends into the tray recess 4 at the top of the first wall surface 6 and the top of the second wall surface 7 has a bevel 11. A ledge 29 at the top of a rear of the main body 2 of the cassette 1 extends away from the rear. A base 12 of the tray 5 has a plurality of rows of through holes 13. The holes 13 are substantially oblong in shape along the row and the rows extend across the width of the tray 5.

There are four protrusions 14 or standoff features extending from the writing surface 3 of the main body 2 of the cassette 1 wherein each protrusion 14 is adjacent a respective corner of the writing surface 3. Thus, there is a first pair 15 of protrusions 14 adjacent a first shorter edge of the rectangular writing surface 3 and there is a second pair 16 of protrusions 14 adjacent an opposite second shorter edge of the rectangular writing surface 3. The two pairs 15, 16 of protrusions 14 are spaced apart to define a print area 30 (shown in chain dot) on the writing surface 3 for a print head of a thermal printer to print on. Each protrusion 14 has substantially the same height from the writing surface 3 and has a rounded profile (see also FIG. 7) wherein the protrusion 14 may be in the form of a dome.

The tray 5 is covered by a removable rectangular lid 17 which has a perimeter edge surface formed from first and second opposed shorter edge surfaces 18, 19 interconnected by first and second opposed longer edge surfaces 20, 21. A pair of recesses 22 extends into a lower part of the first shorter edge surface 18 and are spaced and shaped to receive the respective tabs 10 of the laboratory sample cassette 1 when the lid 17 is placed on the cassette 1. The second shorter edge surface 19 is inclined to correspond with the bevel 11 of the second wall surface 7 of the tray 5 of the cassette 1 when the lid 17 is placed on the cassette 1. The lid 17 has a plurality of rows of through holes 23. The holes 23 are substantially oblong in shape along the row and the rows extend across the width of the lid 17. The lid holes 23 substantially align with the tray base holes 13 when the lid 17 is placed on the cassette 1.

The laboratory sample cassette 1 including the protrusions 14 is formed by injection moulding as is the lid 17.

An example of use of the laboratory sample cassette 1 will now be described.

Figure 3:
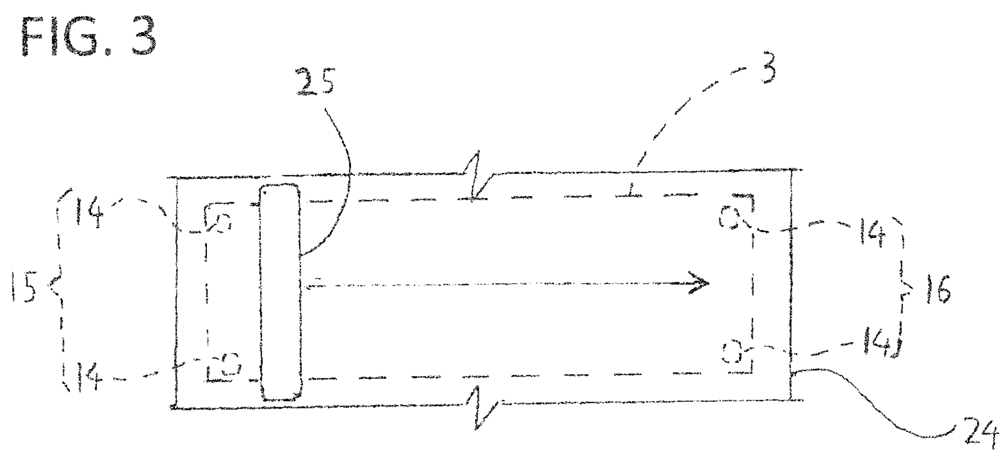
FIG. 3 is a plan view of a writing surface of the laboratory sample cassette with a thermal tape over it and a thermal print head on the tape.

Referring to FIG. 3, the laboratory sample cassette 1 is placed against a thermal printer so that thermal tape 24 of the printer runs across the length of the writing surface 3 and over the first and second pairs 15, 16 of protrusions 14. The rounded profile of the protrusions 14 prevents them from damaging the thermal tape 24 placed over them. A thermal print head 25 of the printer pushes the tape 24 against the writing surface 3 just in from the first pair 15 of protrusions 14 and moves towards the second pair 16 of protrusions 14 to mark the writing surface 3 before the thermal print head 25 moves away from the writing surface 3. The cassette 1 is then ejected from the printer.

Figure 4:
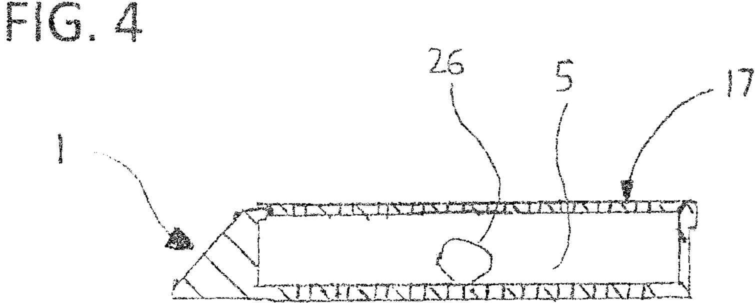
FIG. 4 is a longitudinal sectional view of the laboratory sample cassette containing a tissue sample.

Referring to FIG. 4, a tissue sample 26 is placed in the tray 5 and the lid 17 is placed over the tray 5 to hold and protect the tissue sample 26 in the laboratory sample cassette 1. The cassette 1 is passed through a series of solvents and solutions which ensures that the tissue sample 26 is dehydrated and cleaned so that it is ready for the process of paraffin wax embedding.

This process involves placing the laboratory sample cassette 1 in a wax bath. The cassette 1 is then taken out of the wax bath, the lid 17 is removed and the tissue sample 26 is taken out of the tray 5.

Figure 5:
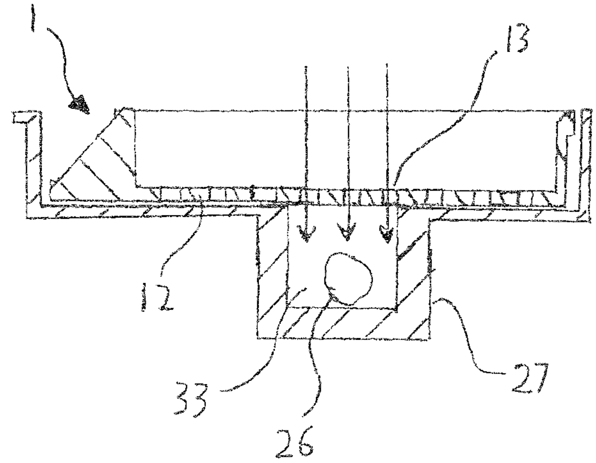
FIG. 5 is a longitudinal sectional view of the laboratory sample cassette on a mould.

Referring to FIG. 5, the tissue sample 26 is placed in a recess 33 in a base of a mould 27, and the cassette 1 is placed in the mould 27 above the recess 33. Molten wax is poured into the mould 27 and passes through the holes 13 in the base 12 of the tray 5 and into the recess 33. The wax is left to cool in the mould 27 and the mould 27 is then removed from the underside of the cassette 1.

Figure 6:
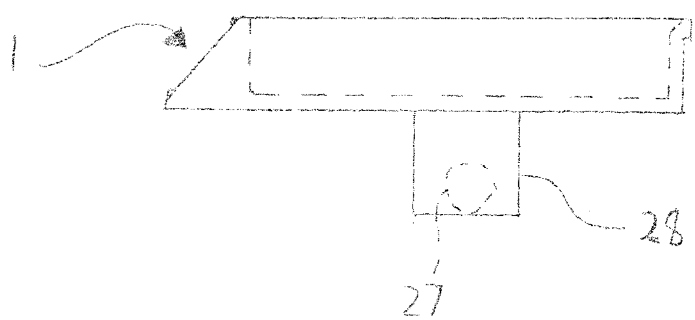
FIG. 6 is a side elevational view of the laboratory sample cassette with a block of wax on its underside.

Referring to FIG. 6, when the mould 27 has been removed, a solid block of wax 28, which has been formed by the mould recess 33, is left on the underside of the laboratory sample cassette 1 wherein the wax block 28 contains the tissue sample 26.

Figure 7:
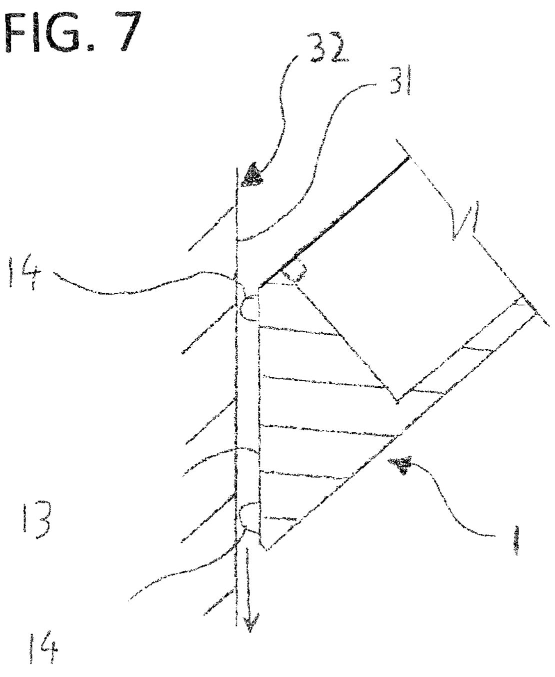
FIG. 7 is a longitudinal sectional view of a portion of the laboratory sample cassette against a flat surface of a heated metal block.

As a result of the wax bath and the pouring of molten wax into the mould 27, the writing surface 3 and other surfaces of the cassette may be at least partially covered by wax. Referring to FIG. 7, to remove any wax on the writing surface 3, the laboratory sample cassette 1 is placed against a flat surface 31 of a heated metal block 32 so that the four protrusions 14 of the writing surface 3 hold the writing surface 3 parallel to the flat surface 31. Wax on the writing surface 3 melts and runs off the writing surface 3 between the protrusions 14.

Other surfaces of the laboratory sample cassette 1 may also be placed against the heated metal block 32 to remove any wax from those surfaces which could otherwise make it difficult to fit the cassette 1 later into a microtome chuck. Once the cassette 1 with the block of wax 28 containing the tissue sample 27 on its underside is placed in the microtome chuck, a blade of the microtome is then used to cut the wax block 28 containing the tissue sample 27 into thin slices. These thin slices are mounted on laboratory slides so that sections of the tissue sample 27 can be analyzed.

The height of the protrusions 14 from the writing surface 3 is sufficiently low so that the protrusions 14 do not cause the thermal tape 25 to be held away from the writing surface 3 during the printing process whilst also being sufficiently high to provide a gap between the writing surface 3 and the flat surface 31 of the heated metal block 32 to enable wax to melt and run off the writing surface 3. In a specific example of a preferred embodiment, the height of each protrusion 14 from the writing surface 3 is in the range of 0.05 mm to 1.5 mm. However, the protrusion 14 may be up to 3 mm high. Also, each protrusion 14 has a width at its base on the writing surface 3 in the range of 0.1 mm to 1 mm. However, the protrusion 14 may be up to 3 mm wide.

Figure 8:
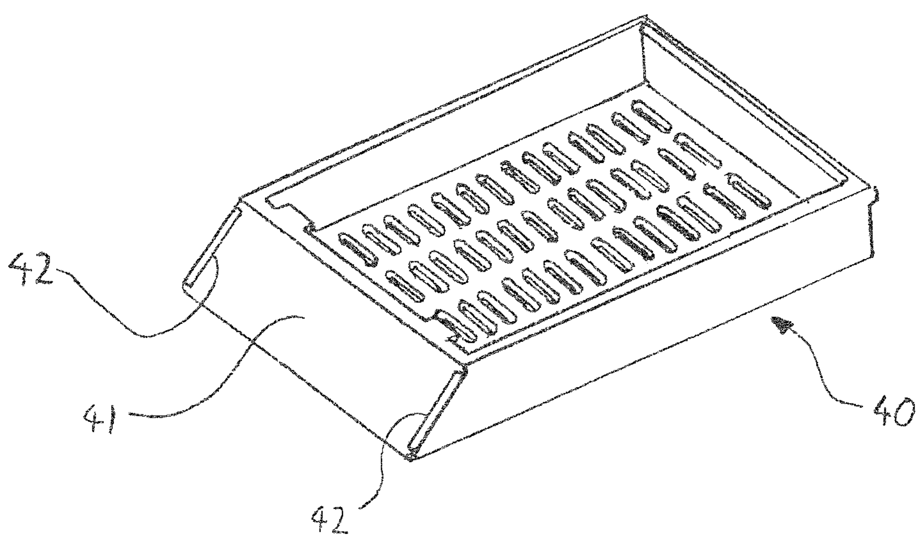
FIG. 8 is a perspective view of a modified laboratory sample cassette.

A modified laboratory sample cassette 40 is illustrated in FIG. 8, wherein the rectangular writing surface 41 has two ribs 42 instead of four protrusions, and the lid has been omitted. Each rib 42 extends substantially parallel to and adjacent a respective opposite shorter edge of the writing surface 41 and has substantially the same height from the writing surface 41. Each rib 42 also has a rounded profile.

Similar to the pairs of protrusion of the laboratory sample cassette 1, the ribs 42 of the modified laboratory sample cassette 40 are spaced apart to define a print area on the writing surface 41 for the print head 25 of a thermal printer to print on.

Figure 9:
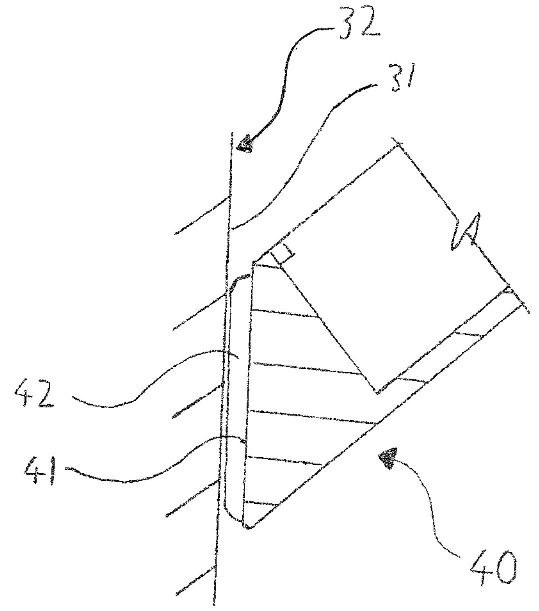
FIG. 9 is a longitudinal sectional view of a portion of the modified laboratory sample cassette against the flat surface of the heated metal block.

During processing, any wax on the writing surface 41 is removed by placing the laboratory sample cassette 40 against the flat surface 31 of the heated metal block 32 so that the two ribs 42 of the writing surface hold the writing surface 41 parallel to the flat surface (see FIG. 9). Wax on the writing surface 41 melts and runs off the writing surface 41 between the ribs 42.

Whilst embodiments have been described, it will be understood that various modifications may be made without departing from the scope of the claimed invention. The laboratory sample cassettes 1, 40 and lid 17 described are examples and there can be other designs of the cassette and lid which fall within the scope of the claimed invention.

The invention claimed is:

1. A method of enabling wax to melt from a marking surface on a main body of a monolithic tissue processing laboratory sample cassette comprising the main body, a recess configured to contain a tissue sample, and a plurality of protrusions including at least a first protrusion and a second protrusion, each of the protrusions extending from the marking surface by substantially the same distance, the method comprising:

enabling the wax to melt from the marking surface by engaging the plurality of protrusions to a flat heating surface such that the marking surface is substantially parallel to the flat heating surface.

2. The method of claim 1, further comprising:

melting the wax; and removing the melted wax from the marking surface.

3. The method of claim 1, further comprising marking the marking surface.

4. The method of claim 1, wherein each protrusion has a rounded profile.

5. The method of claim 1, wherein each protrusion extends from the marking surface by substantially the same distance, the distance being between 0.05 mm and 3 mm.

6. The method of claim 1, wherein the monolithic tissue processing laboratory sample cassette does not include additional protrusions other than the first protrusion and the second protrusion.

7. The method of claim 1, wherein the monolithic tissue processing laboratory sample cassette further comprises a third protrusion and a fourth protrusion.

8. The method of claim 7, wherein the marking surface includes a plurality of corners and each protrusion is adjacent a corresponding corner.

9. The method of claim 1, wherein the monolithic tissue processing laboratory sample cassette is formed as a monolithic structure by an injection molded process.

10. The method of claim 1, wherein the marking surface is rectangular.

11. The method of claim 1, wherein each protrusion has a corresponding base width on the marking surface between 0.1 mm and 3 mm.

12. The method of claim 1, wherein the main body further comprises a main body bottom and the marking surface is disposed at an acute angle relative to the main body bottom.

13. The method of claim 1, wherein the flat heating surface is part of a metal block.

* * * * *